US009005975B2

(12) United States Patent
Okano et al.

(10) Patent No.: US 9,005,975 B2
(45) Date of Patent: Apr. 14, 2015

(54) METHOD FOR SELECTING CLONE OF INDUCED PLURIPOTENT STEM CELLS

(75) Inventors: Hideyuki Okano, Tokyo (JP); Yohei Okada, Tokyo (JP); Shinya Yamanaka, Kyoto (JP); Kyoko Miura, Kyoto (JP)

(73) Assignee: Kyoto University, Kyoto (JP)

( * ) Notice: Subject to any disclaimer, the term of this patent is extended or adjusted under 35 U.S.C. 154(b) by 286 days.

(21) Appl. No.: 13/375,099

(22) PCT Filed: May 28, 2010

(86) PCT No.: PCT/JP2010/003620
§ 371 (c)(1),
(2), (4) Date: Jan. 31, 2012

(87) PCT Pub. No.: WO2010/137348
PCT Pub. Date: Dec. 2, 2010

(65) Prior Publication Data
US 2012/0129172 A1    May 24, 2012

Related U.S. Application Data

(60) Provisional application No. 61/217,362, filed on May 29, 2009.

(51) Int. Cl.
*C12N 15/05* (2006.01)
*C12N 15/00* (2006.01)
*C12N 5/074* (2010.01)
*C12Q 1/68* (2006.01)

(52) U.S. Cl.
CPC ............ *C12Q 1/6881* (2013.01); *C12N 5/0696* (2013.01); *C12N 2510/00* (2013.01); *C12Q 2600/158* (2013.01)

(58) Field of Classification Search
USPC ................................................ 435/325, 455
See application file for complete search history.

(56) References Cited

U.S. PATENT DOCUMENTS

| 8,048,999 | B2 * | 11/2011 | Yamanaka et al. | ............ 536/23.5 |
| 8,058,065 | B2 * | 11/2011 | Yamanaka et al. | ............ 435/377 |
| 8,129,187 | B2 * | 3/2012 | Yamanaka et al. | ............ 435/377 |
| 8,278,104 | B2 * | 10/2012 | Yamanaka et al. | ............ 435/377 |
| 2011/0183350 | A1 | 7/2011 | Okano et al. | |

FOREIGN PATENT DOCUMENTS

| EP | 2072618 | * | 5/2009 |
| WO | WO 03/095629 A1 | | 11/2003 |
| WO | WO 2007/047581 A2 | | 4/2007 |
| WO | WO 2007/097492 A1 | | 8/2007 |
| WO | WO 2009/077134 | * | 4/2009 |
| WO | WO 2010/016253 A1 | | 2/2010 |
| WO | WO 2011/158960 A1 | | 12/2011 |

OTHER PUBLICATIONS

Jaenisch (Cell, Feb. 22, 2008, vol. 132, p. 567-582).*
Takahashi (Cell, 2006, vol. 126:663-676).*
Takahashi (Cell, 2007, vol. 131: 861-872).*
Okita (Nature, Jul. 19, 2007, vol. 448, p. 313-317).*
Yu (Science, 2007, vol. 318, p. 1917-1920).*
Blelloch (Cell Stem Cell, Sep. 13, 2007, vol. 1, p. 245-247).*
Nakagawa (Nat Biotechnol, Jan. 2008, vol. 26: 101-106).*
Aoi (Science, Aug. 2008, vol. 321, p. 699-702; published online Feb. 14, 2008).*
Okita (Science, Nov. 7, 2008, vol. 322, p. 949-953).*
Feng (Cell Stem Cell, Apr. 3, 2009, vol. 4, p. 301-312).*
Kaji (Nature, Apr. 9, 2009, vol. 458, p. 771-776).*
Woltjen (Nature, Apr. 9, 2009, vol. 458, No. 7239, p. 766-770).*
Yu (Science, May 8, 2009, vol. 324, No. 5928, p. 797-801).*
Loh (Blood, May 28, 2009, vol. 113, No. 22, p. 5476-5479).*
Oct4 description, Wikipedia, 2014.*
Nanog description, Wikipedia, 2014.*
Fukuda et al., *Stem Cells*, 24: 763-771 (2006).
Martin-Ibanez et al., *Journal of Neuroscience Research*, 85(12): 2686-2701 (2007).
Piestun et al., *Biochemical and Biophysical Research Communications*, 343(1): 279-285 (2006).
European Patent Office, Supplementary European Search Report in European Patent Application No. EP 09 80 4740 (Apr. 2, 2012).
Japanese Patent Office, International Preliminary Report on Patentability in International Patent Application No. PCT/JP2009/003755 (Dec. 21, 2010).
Japanese Patent Office, International Preliminary Report on Patentability in International Patent Application No. PCT/JP2010/003620 (Sep. 6, 2011).
Aoi, Takahashi, Proceedings of the 27th Meeting of the Japan Human Cell Society, A4, Item S1-4 (2009).
Aoi et al., *Science*, 321: 699-702 (2008).
Chung et al., *Journal of Neurochem.*, 97(5): 1467-1480 (2006).
Eiges et al., *Current Biology*, 11(7): 514-518 (2001).
Hentze et al., *Trends in Biotechnology*, 25(1): 24-32 (2007).
Meissner et al, *Nature Biotechnology*, 25(10): 1177-1181 (2007).
Miura et al., *Nature Biotechnology*, 27(8): 743-745 (2009).
Nakagawa et al., *Nature Biotechnology*, 26(1): 101-106 (2008).
Okada et al., *Stem Cells*, 26(12): 3086-3098 (2008).
Okano et al., "A Study of Imaging and Therapy" in Amyotrophic Lateral Sclerosis (ALS) Annual Report 2007: Summary of the Research, pp. 17-19 (Mar. 2008).
Okita et al., *Nature*, 448(7151): 313-317 (2007).
Osafune et al., *Nature Biotechnology*, 26(3): 313-315 (2008).
Takahashi et al., *Cell*, 126(4): 663-676 (2006).

(Continued)

*Primary Examiner* — Michael C. Wilson
(74) *Attorney, Agent, or Firm* — Leydig, Voit & Mayer, Ltd.

(57) ABSTRACT

To efficiently identify and select a clone from clones of induced pluripotent stem cells (iPS cell) having low tumor formation rate in vivo when allowed to differentiate and transplanted in a living body, iPS cells of the clones are induced to differentiate, undifferentiated cells among the cells after the induction of differentiation are detected, and a clone having the content of the undifferentiated cell below a control is selected.

4 Claims, 6 Drawing Sheets

(56) References Cited

OTHER PUBLICATIONS

Tanabe et al., *Regenerative Medicine* (*Saisei Iryo*), 7(2): 83-89 (2008).
Wernig et al., *Cell Stem Cell*, 2(1): 10-12 (2008).
Wernig et al., *Nature*, 448(7151): 318-324 (2007).
Wernig et al., *Proc. Natl. Acad. Sci. USA*, 105(15): 5856-5861 (2008).
Yamanaka, *Shinya Cell*, 137(1): 13-17 (2009).
Japanese Patent Office, International Search Report in International Patent Application No. PCT/JP2009/003755 (Nov. 2, 2009).
Japanese Patent Office, International Search Report in International Patent Application No. PCT/JP2010/003620 (Aug. 24, 2010).
Cunningham et al., *Society for Neuroscience Abstracts*, 26(1-2): Abstract No. 604.13 (2000).
Do et al., *Reprod. Fertil. Dev.*, 17(1-2): 143-149 (2005).
Hitoshi et al., *Genes & Development*, 16: 846-858 (2002).

\* cited by examiner

Fig. 6

SEQUENCE LISTING

<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: PCR primer

<400> SEQUENCE: 1
tctttccacc aggccccgg ctc                                          23

<210> SEQ ID NO 2
<211> LENGTH: 23
<212> TYPE: DNA
<213> ORGANISM: Artificial Sequence
<220> FEATURE:
<223> OTHER INFORMATION: PCR primer

<400> SEQUENCE: 2
tgcgggcgga catggggaga tcc                                          23

<210> SEQ ID NO 3
<211> LENGTH: 24
<212> TYPE: DNA
<213> ORGANISM: Artificial Sequence
<220> FEATURE:

```
<223> OTHER INFORMATION: PCR primer

<400> SEQUENCE: 3
ttgggctaga gaaggatgtg gttc                                            24

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
ttatcgtcga ccactgtgct gctg                                            24

<210> SEQ ID NO 5
<211> LENGTH: 28
<212> TYPE: DNA
<213> ORGANISM: Artificial Sequence
<220> FEATURE:
<223> OTHER INFORMATION: PCR primer

<400> SEQUENCE: 5
tgacctaact cgaggaggag ctggaatc                                        28

<210> SEQ ID NO 6
<211> LENGTH: 28
<212> TYPE: DNA
<213> ORGANISM: Artificial Sequence
<220> FEATURE:
<223> OTHER INFORMATION: PCR primer

<400> SEQUENCE: 6
ttatgcacca gagtttcgaa gctgttcg                                        28

<210> SEQ ID NO 7
<211> LENGTH: 24
<212> TYPE: DNA
<213> ORGANISM: Artificial Sequence
<220> FEATURE:
<223> OTHER INFORMATION: PCR primer

<400> SEQUENCE: 7
cagaggagga acgagctgaa gcgc                                            24

<210> SEQ ID NO 8
<211> LENGTH: 24
<212> TYPE: DNA
<213> ORGANISM: Artificial Sequence
<220> FEATURE:
<223> OTHER INFORMATION: PCR primer

<400> SEQUENCE: 8
ttatcgtcga ccactgtgct gctg                                            24

<210> SEQ ID NO 9
<211> LENGTH: 23
<212> TYPE: DNA
<213> ORGANISM: Artificial Sequence
<220> FEATURE:
<223> OTHER INFORMATION: PCR primer

<400> SEQUENCE: 9
tagagctaga ctccgggcga tga                                             23
```

```
<210> SEQ ID NO 10
<211> LENGTH: 23
<212> TYPE: DNA
<213> ORGANISM: Artificial Sequence
<220> FEATURE:
<223> OTHER INFORMATION: PCR primer

<400> SEQUENCE: 10
ttgccttaaa caagaccacg aaa                                             23

<210> SEQ ID NO 11
<211> LENGTH: 24
<212> TYPE: DNA
<213> ORGANISM: Artificial Sequence
<220> FEATURE:
<223> OTHER INFORMATION: PCR primer

<400> SEQUENCE: 11
ggttacctct tcctcccact ccag                                            24

<210> SEQ ID NO 12
<211> LENGTH: 24
<212> TYPE: DNA
<213> ORGANISM: Artificial Sequence
<220> FEATURE:
<223> OTHER INFORMATION: PCR primer

<400> SEQUENCE: 12
ttatcgtcga ccactgtgct gctg                                            24

<210> SEQ ID NO 13
<211> LENGTH: 23
<212> TYPE: DNA
<213> ORGANISM: Artificial Sequence
<220> FEATURE:
<223> OTHER INFORMATION: PCR primer

<400> SEQUENCE: 13
ccaacttgaa catgcccgga ctt                                             23

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
tctgcttaaa ggcatacttg gga                                             23

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
gcgaactcac acaggcgaga aacc                                            24

<210> SEQ ID NO 16
<211> LENGTH: 24
<212> TYPE: DNA
<213> ORGANISM: Artificial Sequence
<220> FEATURE:
<223> OTHER INFORMATION: PCR primer
```

```
<400> SEQUENCE: 16
ttatcgtcga ccactgtgct gctg                                            24

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
cgtgggccgc cctaggcacc a                                               21

<210> SEQ ID NO 18
<211> LENGTH: 21
<212> TYPE: DNA
<213> ORGANISM: Artificial Sequence
<220> FEATURE:
<223> OTHER INFORMATION: PCR primer

<400> SEQUENCE: 18
ttggccttag ggttcagggg g                                               21
```

METHOD FOR SELECTING CLONE OF INDUCED PLURIPOTENT STEM CELLS

CROSS REFERENCE TO RELATED APPLICATIONS

This application claims the benefit of priority to U.S. Provisional Patent Application No. 61/217,362, filed on May 29, 2009, which is incorporated herein by reference. All of the documents cited in the specification is also incorporated herein by reference.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,569 bytes ASCII (Text) file named "709385SequenceListing.txt," created Nov. 29, 2011.

TECHNICAL FIELD

The present invention relates to methods for selecting a clone of induced pluripotent stem cells, and the clones selected by the selection methods.

BACKGROUND ART

The induced pluripotent stem cells (iPS cells) can be produced by introducing reprogramming factors into somatic cells (K. Takahashi and S. Yamanaka, Cell 126 (4), 663, 2006; WO2007/069666). The iPS cells thus produced have been confirmed to possess pluripotency, for example, by the fact that iPS cells contribute to the germline of chimeric mice (K. Okita, et al., Nature 448 (7151), 313, 2007; M. Wernig, et al., Nature 448 (7151), 318, 2007). Since the iPS cells can be produced by using cells derived from a patient to be treated and then induced to differentiate into cells of intended tissues, they are expected in the field of regenerative medicine to serve as a transplantation material free from rejection.

However, in chimeric mice derived from the iPS cells thus produced and their offsprings, possibility that a tumor is formed due to reactivation of the introduced c-myc gene cannot be denied. Thus, in order to reduce their tumor formation ability, methods without using a retrovirus carrying c-Myc gene have been developed to produce iPS cells, although their efficiency of induction is relatively low (M. Nakagawa, et al., Nat Biotechnol 26 (1), 101, 2008; M. Wernig, et al., Cell Stem Cell 2 (1), 10, 2008; WO2008/118820; WO2009/057831). Nonetheless, in consideration of the high efficiency with using c-Myc, it is more desirable to develop a method for selecting iPS cells with low tumor formation ability while using a retrovirus carrying c-Myc.

Similarly, although various methods have been developed for practical application of producing iPS cells, such as a method of preparing iPS cells adaptable to production of chimeric mice without employing selection by a drug (A. Meissner, et al., Nat Biotechnol 25(10), 1177 2007) and a method of produce iPS cells using cells from various tissues (Aoi, T. et al., Science 321, 699-702, 2008), the iPS cells thus produced are not always suitable for transplantation.

Accordingly, it is expected to establish methods not only for producing iPS cells but also for selecting iPS cells with high safety.

SUMMARY OF INVENTION

Technical Problem

The present invention is intended to provide methods for efficiently identifying and selecting clones of iPS cells having low tumor formation rate in vivo when allowed to differentiate and transplanted in a living body, as well as the clones selected by the methods and kits for the selection.

Solution to Problem

In one embodiment of the present invention, a method for selecting a clone of induced pluripotent stem cells (iPS cells) includes the steps of detecting an undifferentiated cell in the clones after induction of differentiation of the iPS cells, and selecting a clone based on the result of the detection. In the step of detecting an undifferentiated cell, formation of teratoma may be examined, or promoter activity of an undifferentiated cell-specific gene may be detected, and more preferably a content of cells in which the promoter activity is detected in the clone may be measured. The induction of differentiation may include allowing the iPS cells of the clones to form a primary neurosphere or a secondary neurosphere. In the step of detecting the promoter activity, the iPS cells may have a marker gene whose expression is regulated by the promoter of the undifferentiated cell-specific gene, wherein expression of the marker gene may be detected. The marker gene preferably encodes a fluorescent protein, a luminescent protein or an enzyme. In the step of selecting the clone, expression of an endogenous undifferentiated cell-specific gene may be detected. The undifferentiated cell-specific gene may be, but not limited to, Nanog gene.

In the step of selecting iPS cells, a content of cells where transcription of an undifferentiated cell-specific gene is activated in the clones may be measured in multiple times, and a clone of iPS cells in which an average of the measurements is less than 0.042% or the measurements are less than 0.066% in all generations of the iPS cells examined may be selected.

Another embodiment of the present invention provides a method for producing a clone of iPS cells, comprising the step of selecting a clone from clones of iPS cells by any one of the abovementioned methods.

Another embodiment of the present invention provides a clone of iPS cells selected by any one of the abovementioned methods.

In a further embodiment of the present invention, a kit for selecting a clone of iPS cells contains a reagent to detect promoter activity of an undifferentiated cell-specific gene. The reagent may detect a transcription product transcribed from the undifferentiated cell-specific gene or a gene encoding a fluorescent protein, a luminescent protein or an enzyme, or a reagent to detect a peptide translated from the transcription product. The undifferentiated cell-specific gene may be, but not limited to, Nanog gene.

The iPS cells from which the clone is selected may have been obtained by introducing at least one gene in a gene family selected from the group consisting of Oct gene family, Sox gene family, Klf gene family, Myc gene family, Nanog gene, Sall gene family and Lin28 gene. Preferably, the member of the Oct gene family is Oct3/4; the member of the Sox gene family is Sox2; the member of the Klf gene family is Klf4; the member of the Myc gene family is c-Myc or L-Myc; and the member of the Sall gene family is Sall4 or Sall1. More preferably, the iPS cells have been obtained by introducing Oct3/4 gene, Sox2 gene, Klf4 gene and c-myc gene.

Advantageous Effects of Invention

The present invention can provide methods for efficiently identifying and selecting clones of iPS cells with high safety, as well as clones selected by the methods.

BRIEF DESCRIPTION OF DRAWINGS

FIG. 6 shows expression of introduced genes in SNSs and teratomas. RT-PCR analyses of RNAs isolated from undifferentiated cells (Un.), SNSs derived from cell clones or teratomas (178B5-MEF-iPS, 256H13-TTF-iPS, 256H17-TTF-iPS) by using primer pairs for amplifying either of coding regions of four introduced genes ("total"), a transcript from an endogenous gene only (endo), or a transcript from an introduced gene only (tg). Clone 4-3, a TTF-Fbxo15-iPS cell, was used as a positive control for expression of an introduced gene.

DESCRIPTION OF EMBODIMENTS

Figure 1:
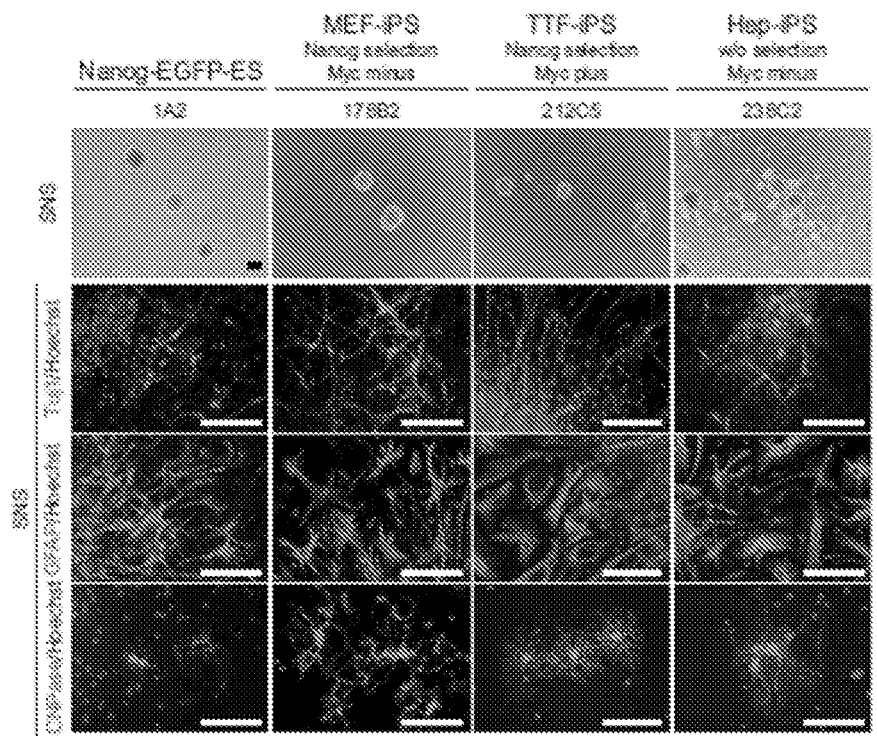
FIG. 1 shows formation of SNSs from mouse iPS cells. (a) Photographs of secondary neurospheres derived from ES cells (1A2), MEF-iPS cells (178B2), TTF-iPS cells (212C5) or Hep-iPS cells (238C2). Scale bar=200 um. (b) Immunohistochemical analyses of Tuj 1 (a marker for neurons), GFAP (a marker for astrocytes) and CNPase (a marker for oligodendrocytes) in the cells induced to differentiate from SNSs. Scale bar=100 um. (c) Immunohistochemical analyses of neurons (using NeuN), astrocytes (using GFAP) and oligodendrocytes (using APC) in a NOD/SCID mouse at 4 weeks after transplantation of SNSs derived from MEF-iPS cells (38C2). Scale bar=50 um (10 um in the inset).
Figure 1:
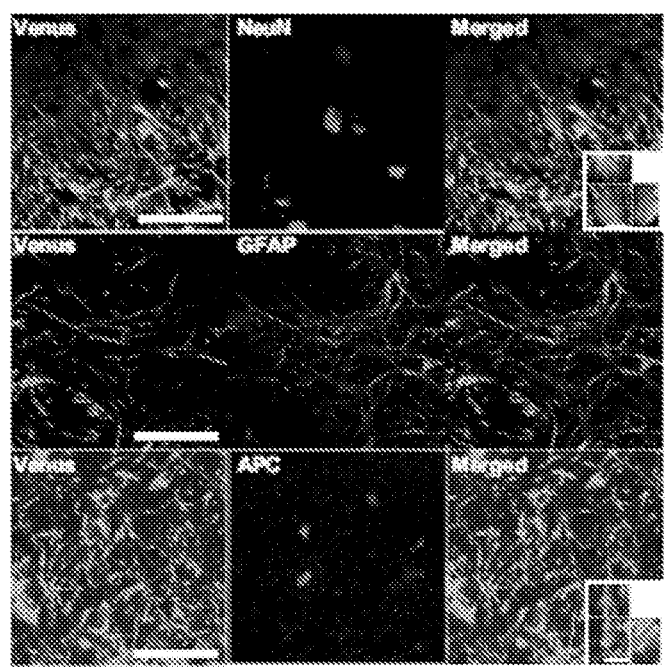

Embodiments of the present invention accomplished based on the above-described findings are hereinafter described in detail by giving examples. Where there is no particular explanations in embodiments or examples, methods described in standard sets of protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., or their modified/changed methods are used. When using a commercial reagent kit or a measuring apparatus, unless otherwise explained, protocols attached to them are used.

The object, characteristics, advantages of the present invention as well as the idea thereof are apparent to those skilled in the art from the descriptions given herein, and the present invention can be easily worked by those skilled in the art based on the descriptions given herein. It is to be understood that the embodiments and specific examples of the invention described hereinbelow are to be taken as preferred examples of the present invention. These descriptions are only for illustrative and explanatory purposes and are not intended to limit the invention to these embodiments or examples. It is further apparent to those skilled in the art that various changes and modifications may be made based on the descriptions given herein within the intent and scope of the present invention disclosed herein.

==Induced Pluripotent Stem Cells==

An induced pluripotent stem cell (iPS cell) refers to a cell having pluripotency and self-reproducing ability, which is artificially induced by reprogramming a differentiated cell other than germline cells (such as egg cells, sperm cells and their precursor cells such as oogonia and spermatogonia) or undifferentiated cells derived from embryos at early stages of development (such as embryonic stem cells). The differentiated cell may be derived from an embryo, a fetus, or an adult, and may originate from any animal species, such as mice or humans. The characteristics of the differentiated cell are not particularly limited as long as the cell has at least partly lost endogenous totipotency of a fertilized cell. Examples of the differentiated cell include fibroblasts, epithelial cells, hepatocytes, etc.

The method for the reprogramming is not particularly limited, but in a preferred method cells are induced to obtain pluripotency and self-reproduction ability by introducing a nuclear reprogramming factor. For example, any of the reprogramming methods described in WO2005/080598, WO2007/069666, WO2008/118820 and WO2009/057831 may be used. The disclosures of these publications are incorporated herein by reference.

The nuclear reprogramming factor is not particularly limited, but preferred is at least one product of a gene in a family selected from each of the Oct gene family, Klf gene family, Sox gene family, Myc gene family, Sall gene family, Nanog gene family (mouse NM_028016, human NM_024865) and Lin gene family. The genes belonging to the Oct gene family include Oct3/4 (mouse NM_013633, human NM_002701), Oct1A (mouse NM_198934, human NM_002697) and Oct6 (mouse NM_011141, human NM_002699); those belonging to the Klf gene family include Klf1 (mouse NM_010635, human NM_006563), Klf2 (mouse NM_008452, human NM_016270), Klf4 (mouse NM_010637, human NM_004235) and Klf5 (mouse NM_009769, human NM_001730); those belonging to the Sox gene family include Sox1 (mouse NM_009233, human NM_005986), Sox2 (mouse NM_011443, human NM_003106), Sox3 (mouse NM_009237, human NM_005634), Sox2 (mouse NM_011446, human NM_031439), Sox15 (mouse NM_009235, human NM_006942), Sox17 (mouse NM_011441, human NM_022454) and Sox18 (mouse NM_009236, human NM_018419); those belonging to the Myc gene family include c-Myc(mouse NM_010849, human NM_002467), N-Myc (mouse NM_008709, human NM_005378) and L-Myc (mouse NM_008506, human NM_001033081); those belonging to the Sall gene family include Sall1 (mouse NM_021390, human NM_002968) and Sal4 (mouse NM_175303, human NM_020436); and those belonging to the Lin gene family include Lin28 (mouse NM_145833, human NM_024674) and Lin28b (mouse NM_001031772, human NM_001004317). As the nuclear reprogramming factor, other kinds of gene products may also be used, and examples include an immortalization-inducing factor.

More preferably, the nuclear reprogramming factor may include at least a product of one or more genes selected from Oct3/4 gene, Klf4 gene, Sox2 gene, c-Myc gene, L-Myc gene, Sall4 gene, Sall1 gene, Nanog gene and Lin28 gene.

While these genes are herein represented by mouse and human sequences with reference to their Accession Numbers registered at the National Center for Biotechnology Information (NCBI), they are all highly conserved among the vertebrates, and therefore a gene represented herein includes its homologues unless a name of a particular animal is indicated. Moreover, mutated genes including those with polymorphism are also encompassed as long as they have a function comparable to that of the wild-type gene product.

==Methods for Producing iPS Cells==

In order to produce iPS cells by using nuclear reprogramming factors, they are preferably introduced into a somatic cell. The number of nuclear reprogramming factors to be included is two, three, preferably four, or more than four. A preferable combination of the factors is either the combination of Oct3/4 gene, Sox2 gene and Klf4 gene, or the combination of Oct3/4 gene, Sox2 gene, Klf4 gene and c-myc gene.

In order to introduce a nuclear reprogramming factor, in the case where it is a protein functioning in a cell, a gene encoding the protein is preferably incorporated into an expression vector, which is introduced into a target differentiated cell such as a somatic cell, so that the protein is intracellularly expressed (the gene transduction method). The expression vector to be used is not particularly limited, but preferred examples include plasmid vectors, viral vectors and artificial chromosome vectors (Suzuki N. et al., J. Biol. Chem. 281(36):26615, 2006), and preferred examples of the viral vectors include adenovirus vectors, Sendai virus vectors, retrovirus vectors and lentivirus vectors. Alternatively, the protein may be introduced into cells by binding a peptide called protein transduction domain (PTD) to the protein, which is added to a culture medium (the protein transduction method). Also, the protein can be introduced by, for example, utilizing any of various protein introducing agents (such as Chariot™ and Bioporter™) for introducing a purified protein. In the case where the factor is a protein secreted extracellularly, the factor may be added to a medium for culturing differentiated cells during the production of iPS cells. If any of the nuclear reprogramming factors is expressed in the differentiated cells to be reprogrammed, such factors do not need to be introduced exogenously.

In some cases, a cytokine or a chemical compound may be added for the purpose of substituting a nuclear reprogramming factor or for the purpose of improving the efficiency of induction. Examples of the cytokine include SCF (stem cell factor), bFGF, Wnt family and LIF (leukemia inhibitory factor), and examples of the chemical compound include histone deacetylase inhibitor, DNA methylation inhibitor, MEK inhibitor, GSK3beta inhibitor TGF receptor inhibitor and ROCK inhibitor (WO 2009/117439).

After the reprogramming factors are introduced into somatic cells, the cells may be transferred onto feeder cells and cultured. The feeder cells are not particularly limited, but examples include mouse embryonic fibroblasts (MEFs). Media preferably used for the culture include those suitable for culturing cells of the animal species from which the somatic cells are derived, and in the case of human cells for example, a preferred medium is the DMEM/F12 medium supplemented with 20% serum substitute, 2 mM L-glutamine, $1\times10^{-4}$ M non-essential amino acids, $1\times10^{-4}$ M 2-mercaptoethanol, 0.5% penicillin and streptomycin, and 4 ng/ml recombinant human basic fibroblast growth factor (bFGF).

The iPS cells are then isolated from the differentiated cells to which the nuclear reprogramming factors have been introduced by, foe example, selecting cells expressing an undifferentiated cell-specific gene or utilizing morphology of the cells as a marker. The method for selecting cells expressing the undifferentiated cell-specific gene is not particularly limited. In the case where the undifferentiated cell-specific gene encodes an intracellular protein, one of marker genes, such as GFP gene, galactosidase gene and drug resistance genes such as neomycin resistance gene, hygromycin resistance gene and puromycin resistance gene, may be knocked-in to the downstream of a promoter of the undifferentiated cell-specific gene to be expressed as a fusion protein, and cells expressing the marker gene may be selected. In the case where the marker is a drug resistance gene, the desired cells can be easily isolated by a selection using the drug. In the case where the undifferentiated cell-specific gene encodes a membrane protein, cells expressing the protein can be selected by using a specific antibody to the protein or by utilizing an enzymatic activity of the protein. It should be noted that an undifferentiated cell-specific gene as used herein indicates a gene specifically expressed in an embryonic stem cell (ES cell) and known to those skilled in the art, and examples include those disclosed in, for example, WO2005/080598, WO2007/069666, WO2008/118820, WO2009/057831 and Nat Biotechnol. 25, 803, 2007. The undifferentiated cell-specific gene is selected preferably from a group consisting of Oct3/4, Sox2, Nanog, Lin28, Rex1, UTF1, Eras, Fgf4, TDGF, Cripto, Dax1, ESG1, GDF3, Sall14, Fbx15, SSEA-1, SSEA-4, TRA-1-60, TRA-1-81 and alkaline phosphatases (such as TRA-2-54 and TRA-2-49) with consideration of animal species (for example, SSEA-1 is specific for mouse, whereas SSEA-4, TRA-1-60 and TRA-1-81 are specific for human). A preferable undifferentiated cell-specific gene is Fbx15 gene or Nanog gene. In the case where cellular morphology is utilized as a marker, the selection may be conducted by, for example, utilizing formation of colonies as a marker.

Cell populations or cell lines or clones thus isolated from the reprogrammed cells can be used as the iPS cells.

In the present description, the words of cell populations, cell lines and clones are indistinguishable, unless otherwise specified.

==Methods for Identifying/Selecting iPS Cells==

In one embodiment of the present invention, methods are provided for inducing differentiation of cells into a certain cell type and then selecting iPS cells suitable for cell supplement therapy. Specifically, the iPS cells obtained by any of the abovementioned methods are appropriately treated for induction of differentiation, presence of an undifferentiated cell is detected, and the iPS cells are selected based on the result of the detection. The method for detecting an undifferentiated cell may be, but not limited to, the method to examine formation of teratoma from the cells after the induction of differentiation, or the method to detect promoter activity of the undifferentiated cell-specific gene. The iPS cells to be selected are preferably cloned as a population of cells having homogeneous genetic information. The undifferentiated cell-specific gene in this method may be the same as the abovementioned undifferentiated cell-specific gene, and is preferably Nanog gene.

Formation of teratoma may be examined by, for example, transplanting the cells induced to differentiate into an immunodeficient animal, dissecting a tissue at the site of the transplantation at 4 to 45 weeks after the transplantation, and observing a structure of any of fetal or mature tissues of endodermal, mesodermal or ectodermal origin, such as a tumor, cartilage, smooth muscle, mucous gland, respiratory organ, digestive organ and nervous tissue.

The immunodeficient animal may be, but not limited to, nude mice or NOD/SCID mice. The site to which the cells induced to differentiate are transplanted is preferably hypodermis, an inside of testis or corpus striatum.

The method for examining promoter activity of an undifferentiated cell-specific gene is not particularly limited. In the case where the iPS cells have a reporter gene whose expression is regulated by a promoter of an undifferentiated cell-specific gene, expression of the reporter gene may be examined. In an alternative embodiment, the endogenous expression of an undifferentiated cell-specific gene may be examined for promoter activity of the undifferentiated cell-specific gene. Examples of the reporter gene include those encoding fluorescent proteins such as green fluorescent protein (GFP), yellow fluorescent protein (YFP) and blue fluorescent protein (BFP), luminescent proteins such as aequorin, and enzymes such as luciferase, beta-galactosidase, alkaline phosphatase and horse radish peroxidase (HRP).

The iPS cells having a reporter gene whose expression is regulated by a promoter of an undifferentiated cell-specific gene may be produced from differentiated cells by any of methods known to those skilled in the art such as a homologous recombination method, in which the cells are genetically modified by replacing a coding region of the undifferentiated cell-specific gene with a sequence of the reporter gene. Alternatively, the iPS cells may be produced from differentiated cells that have been genetically modified by inserting a sequence of the reporter gene into the locus of the undifferentiated cell-specific gene so that a fusion protein is formed from the protein or a fragment thereof encoded by the undifferentiated cell-specific gene and the protein encoded by the reporter gene. Alternatively, the iPS cells having the reporter gene may be produced by a homologous recombination which involves genetic modification to directly replace the coding region of the undifferentiated cell gene with the reporter gene or to insert the reporter gene into the locus of the undifferentiated cell gene. In an alternative embodiment, the iPS cells having the reporter gene may be produced by introducing, into the iPS cells, a construct containing a nucleotide sequence in which the promoter region of the undifferentiated cell-specific gene is linked with the reporter gene. A DNA fragment containing the promoter region can be isolated from a genomic DNA or a genome library by any of methods known to those skilled in the art based on the result of a promoter analysis on the undifferentiated cell-specific gene to be used. The construct may be prepared using a plasmid vector, a virus vector or an artificial chromosome vector (Suzuki N. et al., J. Biol. Chem. 281(36):26615, 2006).

In the case where expression of the reporter gene or the endogenous undifferentiated cell-specific gene is to be detected, a transcription product (such as hnRNA, mRNA etc.) may be detected by, for example, PCR method, LAMP method or Northern hybridization method. Alternatively, a translation product (such as a peptide, a modified peptide etc.) may be detect by, for example, RIA method, IRMA method, EIA method, ELISA method, LPIA method, CLIA method or immunoblotting method. The transcription product or the translation product is preferably detected in a quantitative manner.

In the method to detect the promoter activity of the undifferentiated cell-specific gene, expression of the reporter gene or the expression of the endogenous undifferentiated cell-specific gene is preferably measured by flow cytometer etc. to quantitate a content of cells having activated promoter of the undifferentiated cell-specific gene in the clone of the cells. In this case, the content of the cells having the activated promoter is calculated as the ratio of such cells in the clone of the cells having been induced to differentiate.

In the case where the content of the cells, which have been induced to differentiate and in which the promoter of the undifferentiated cell-specific gene has been activated, is measured for the selection of a clone of the iPS cells, it is preferable to select clones of the iPS cells in which the content of the cells having the activated promoter is below a control content of cells having the activated promoter in a clone of the cells that would not substantially cause tumor formation when transplanted into a living body. As for the control content, it is preferable to examine tumor formation and examine the content as shown in Table 1 after any of available cell lines is transplanted into a living body, and adopt a content predetermined so that both values of sensitivity and specificity as shown in Table 1 are equal to or more than 0.5, 0.6, 0.7, 0.8, 0.9, 0.95 or 0.99. Preferably, the value of sensitivity is more than 0.9, 0.95, 0.99 or 1. More preferably the values of the sensitivity and specificity are both 1. It should be noted that the both values of the sensitivity and specificity being 1 indicate that tumor formation would not occur if the content is below the determined control content. The cell line to be transplanted is preferably a cell into which an iPS cell or an ES cell is induced to differentiate.

TABLE 1

|  | Number of clones positive for tumor formation | Number of clones negative for tumor formation |
|---|---|---|
| Number of clones in which the content of the cells having the activated promoter is above a control content | A | C |
| Number of clones in which the content of the cells having the activated promoter is below a control content | B | D |
|  | Sensitivity = A/(A + B) | Specificity = D/C + D |

In another embodiment, the detection of the promoter activity may be conducted more than once for each of iPS cells to be examined, in which case an average or a maximum value of the measured contents may be compared with the control content. In the case where the average of the contents is to be compared with the control content, 0.042% is preferably adopted as the control content. In the case where the maximum value of the contents is to be compared with the control content, 0.082%, 0.066%, 0.051% or 0.019% is preferably adopted as the control content. More preferably, 0.066% is adopted as the control content.

In another embodiment where a transcription product or translation product of the undifferentiated cell-specific gene is quantified after the induction of differentiation, amounts of the transcription product or amounts of the translation product in a clone of the iPS cells may be compared with a respective control and the clones having the amount below a control may be selected. As for the control amount of transcription product or translation product, it is preferable to measure tumor formation and the amount of transcription product or translation product as shown in Table 2 after any of available cell line is transplanted into a living body, and adopt a predetermined content with which both values of sensitivity and specificity as shown in Table 2 are equal to or more than 0.5, 0.6, 0.7, 0.8, 0.9, 0.95 or 0.99. Preferably, the value of sensitivity is more than 0.9, 0.95, 0.99 or 1. More preferably the values of the sensitivity and specificity are both 1. It should be noted that both values of the sensitivity and specificity being 1 indicate that tumor formation would not occur if the content is below the predetermined control amount of transcription product or translation product. The cell line to be transplanted is preferably a cell into which an iPS cell or an ES cell is induced to differentiate.

TABLE 2

|  | Number of clones positive for tumor formation | Number of clones negative for tumor formation |
|---|---|---|
| Number of clones with trascription (or translation) products more than control transcription (or tranlsation) products | A | C |
| Number of clones with trascription (or translation) products less than control transcription (or tranlsation) products | B | D |
|  | Sensitivity = A/(A + B) | Specificity = D/C + D |

While the method for inducing differentiation of iPS cells or ES cells is not particularly limited, a preferable method is to induce them to differentiate into neural stem cells or neural progenitor cells by forming neurospheres in which cells are spherically clustered. More preferred is the method to induce the cells to form secondary neurospheres. The induction method for iPS cells into neural stem cells may be the same as the methods used for ES cells and known to those skilled in the art (Okada Y, et al., Stem cells 26 (12), 3086, 2008; Japanese Patent Application Laid-open Publication No. 2002-291469). The iPS cells to be treated may be cultured in suspension in the presence of a low level ($10^{-9}$ M to $10^{-6}$ M) of retinoic acid to thereby induce formation of an embryoid body (EB). Alternatively, the medium for culturing the iPS cells may be supplemented with Noggin protein. Specifically, a culture supernatant from mammalian cultured cells to which Xenopus Noggin has been introduced and induced to transiently express the Noggin protein may be used as is (1 to 50% (v/v)), or a recombinant Noggin protein (about 1 ug/ml) may be added to the medium. Then, the EBs thus obtained are dissociated and cultured in a serum-free medium supplemented with FGF-2 (10 to 100 ng/ml) and B27 to allow them to form primary neurospheres. Further, the primary neurospheres may be dissociated to allow them to form secondary neurospheres under the same conditions. The neurosphere dissociation-neurosphere formation step may be repeated to further form higher-order neurospheres.

The clones of the iPS cells thus selected can be used as a material for the cell supplement therapy.

==Kits==

The kit for selecting clones of iPS cells according to the present invention includes a reagent to detect promoter activity of an undifferentiated cell-specific gene.

As described earlier, the examples of the methods for detecting promoter activity of an undifferentiated cell-specific gene include PCR method, LAMP method, Northern hybridization method, RIA method, IRMA method, EIA method, ELISA method, LPIA method, CLIA method and immunoblotting method. Since all of these detection methods have been publicly known, a person skilled in the art can appropriately include a primer, a probe, an antibody, an enzyme substrate, a reagent and/or the like in the kit in accordance with the detection method to be employed. Also, a vector or recombination construct that contains a promoter of an undifferentiated cell-specific gene and a marker gene whose expression is regulated by the promoter may be included. The recombination construct may be produced by any of the methods known to those skilled in the art. In the case where the undifferentiated cell-specific gene is Nanog, the construct may be the targeting vector described in Mitsui K, et al., Cell, 113, 631, 2003, and in the case where the gene is Fbx15, the construct may be the targeting vector described in Tokuzawa Y, et al, Mol Cell Biol., 23(8), 2699, 2003.

EXAMPLES

<Materials and Methods>
<Culture>

Establishment and culture of ES cells and iPS cells were conducted in the conventional methods as described (Takahashi K and Yamanaka S, Cell 126 (4), 663, 2006; Okita K, et al., Nature 448 (7151), 313, 2007; Nakagawa M, et al., Nat Biotechnol 26 (1), 101, 2008; and Aoi, T. et al., Science 321, 699-702, 2008). Following 5 cell lines of established ES cells or iPS cells; 1A2, 212C6, 256D4, 135C6 and 178B5, were subcloned by picking up colonies after weak cell concentration culture. The induction of differentiation into neural cells was conducted in the method by Okada et al. (Okada Y, et al., Stem cells 26 (12), 3086, 2008) with minor modification. In brief, iPS cells were cultured in the presence of $1 \times 10^{-8}$M retinoic acid to form embryoid bodies (EBs). Subsequently, the EBs were dissociated at 6 days after the addition of retinoic acid, and suspension cultured in the Media hormone mix (MHM) supplemented with B27 and 20 ng/ml FGF-2 (Waco) in a culturing flask (Nunc). On day 4 from suspension culture, the suspension cells were transferred from the culturing flask to a Ultra-Low Attachment dish (Corning), and cultured in the same medium for 3 or 4 days. Then primary neurospheres (PNSs) were formed. Subsequently, the prepared PNSs were dissociated by using TrypLESelect and suspension-cultured in the same medium. After 4 days from the suspension culture, the suspension cells were placed on a coverslip coated with poly-L ornithine/fibronectin and cultured in the absence of FGF2 for 5 to 6 days. In this way secondary neurospheres (SNSs) were formed.

<Flow Cytometry>

Undifferentiated iPS cells and iPS-derived SNSs containing Nanog-EGFP reporter (WO2007/069666) were dissociated and subjected to flow cytometry analyses with using FACS Calibur or FACS Aria (both Becton-Dickinson). Dead cells were detected by propidium iodide staining and removed, and the number of EGFP-positive cells was measured as a ratio in viable cells.

<Production of Lentivirus and Infection to Secondary Neurospheres>

For transplantation into a brain of a NOD/SCID mouse, cells were labeled with pCSII-EF-MCS-IRES2-Venus which was constructed by using a third-generation lentivirus vector derived from HIV-1 with inactivated self-propagation (Miyoshi H, et al., J Virol 72 (10), 8150, 1998). For production of lentivirus, HEK-293T cells were transfected with either pCSII-EF-MCS-IRES2-Venus, pCAG-HIVgp and pCMV-VSV-G-RSV-Rev (all in Miyoshi H, et al., J Virol 72 (10), 8150, 1998), and culture supernatant containing respective viral particles was recovered. The viral particles were concentrated by centrifugation at 25000 rpm, 4° C. for 1.5 hour. The concentrated viral particles were added to the culture medium during the formation of SNS from PNS.

<Transplantation into Brain of NOD/SCID Mouse>

The neurospheres introduced with Venus by using the lentivirus (pCSII-EF-MCS-IRES2-Venus) were transplanted by using a glass micropipette on a stereotactic introducer in a conventional method (Ogawa D, et al., J Neurosci Res, 2008). In this method, the tip of the pipette was inserted into a right corpus striatum (1 mm rostral and 2 mm lateral from bregma and 3 mm deep from dura mater) of a 6 week-old female NOD/SCID mouse and 3 ml of the suspension of SNS cells ($2 \times 10^5$ cells) was injected.

Example 1

Differentiation of Respective iPS Cells into Neurons 36 clones of iPS cells were divided according to (1) the origins of iPS cells; i.e. MEF (Mouse Embryonic Fibroblast), TTF (Tail Tip Fibroblast), Hep (Hepatocyte) or Stm (Stomach epithelial cell); (2) with or without introduction of c-Myc-containing retrovirus; and (3) with or without selection in terms of expression of Nanog or Fbxo15. Profiles and results of analyses of each clone are shown in Tables 3 and 4. As control, the following three ES cell clones were used (RF8 (Meiner, V. L. et al., Proc Natl Acad Sci USA., 93(24):14041, 1996); 1A2, a subclone thereof having Nanog-EGFP reporter (Okita K, et al., Nature 448 (7151), 313, 2007); and EB3 having an Oct3/4 blasticidin resistant reporter gene (Mol Cell Biol., 22(5):1526, 2002 and Okada Y, et al., Stem cells 26 (12), 3086, 2008)). When these iPS cells and ES cells were allowed to form neurospheres containing neural stem cells and/or precursor cells (NS/PC), each of the iPS clones and most of the ES cells formed primary neurospheres (PNS) in the presence of FGF2 after formation of embryoid bodies. When the PNS were dissociated and secondary neurospheres were formed (FIG. 1a), three of Hep-iPS clones and one of Stm-iPS clones did not form a SNS (Table 3). The SNSs derived from iPS cells and ES cells were differentiated in vitro into three types of neural cells, i.e. neurons, astrocytes and oligodendrocytes (FIG. 1b). These SNSs survived also in vivo, and differentiated into the three types of neural cells (FIG. 1c). The iPS cells thus possess the potency to differentiate into neural cells as ES cells do, regardless of the cell type of their origin or presence/absence of the c-Myc-containing retrovirus or selection.

TABLE 3

| iPS line | | | | SNS formation | | Transplantation of SNSs | | | | |
|---|---|---|---|---|---|---|---|---|---|---|
| | | | | EGFP+ cells in | Average of EGFP+ cells in | Diameter of teratoma (mm) | | | Analyzed number of | Teratoma+/ |
| Origin | Selection | cMyc | clone's name | Trial | SNSs (%) | SNSs (%) | ≥8.3 | 5.8-8.2 | 0.1-5.7 | 0 | mice | total |
| MEF | Nanog | + | 20D17 | 1st | ND | 0.0454075 | 0 | 0 | 3 | 0 | 3 | 15/21 |
| | | | | 2nd | ND | | 0 | 3 | 2 | 0 | 5 | |
| | | | | 3rd | 0.00363 | | 0 | 0 | 0 | 4 | 4 | |
| | | | | 4th | 0.049 | | 0 | 0 | 0 | 2 | 2 | |
| | | | | 5th | 0.11 | | 0 | 0 | 3 | 0 | 3 | |
| | | | | 6th | 0.019 | | 0 | 0 | 4 | 0 | 4 | |
| | | | 38D2 | 1st | ND | 0.103805 | 0 | 0 | 3 | 0 | 3 | 13/17 |
| | | | | 2nd | ND | | 0 | 1 | 2 | 0 | 3 | |

TABLE 3-continued

| iPS line | | | | SNS formation | | Transplantation of SNSs | | | | | |
|---|---|---|---|---|---|---|---|---|---|---|---|
| | | | | | Average of | | Diameter of teratoma (mm) | | | Analyzed | |
| | | | | EGFP+ | EGFP+ | | | | | number of | Teratoma+/ |
| | | clone's | | cells in | cells in | | | | | | |
| Origin | Selection | cMyc | name | Trial | SNSs (%) | SNSs (%) | ≥8.3 | 5.8-8.2 | 0.1-5.7 | 0 | mice | total |
| | | | | 3rd | 0.026 | | 0 | 0 | 3 | 0 | 3 | |
| | | | | 4th | 0.00143 | | 0 | 0 | 0 | 2 | 2 | |
| | | | | 5th | 0.00779 | | 0 | 0 | 0 | 2 | 2 | |
| | | | | 6th | 0.38 | | 0 | 0 | 4 | 0 | 4 | |
| | | | 38C2 | 1st | ND | 0 | 0 | 0 | 0 | 4 | 4 | 0/17 |
| | | | | 2nd | ND | | 0 | 0 | 0 | 7 | 7 | |
| | | | | 3rd | 0 | | 0 | 0 | 0 | 4 | 4 | |
| | | | | 4th | 0 | | 0 | 0 | 0 | 2 | 2 | |
| | | − | 178B5 | 1st | ND | 0 | 0 | 0 | 0 | 3 | 3 | 0/7 |
| | | | | 2nd | 0 | | 0 | 0 | 0 | 4 | 4 | |
| | | | 178B1 | 1st | 0.0012 | 0.0006 | 0 | 0 | 0 | 3 | 3 | 0/6 |
| | | | | 2nd | 0 | | 0 | 0 | 0 | 3 | 3 | |
| | | | 178B2 | 1st | 0.0012 | 0.0006 | 0 | 0 | 0 | 3 | 3 | 0/6 |
| | | | | 2nd | 0 | | 0 | 0 | 0 | 3 | 3 | |
| | w/o | | 506GN1 | 1st | 0.0052 | 0.0026 | 0 | 0 | 0 | 2 | 2 | 0/4 |
| | | | | 2nd | 0 | | 0 | 0 | 0 | 2 | 2 | |
| | | | 506GN2 | 1st | 0.0719 | 0.03695 | 0 | 0 | 0 | 2 | 2 | 0/4 |
| | | | | 2nd | 0.002 | | 0 | 0 | 0 | 2 | 2 | |
| | | | 506GN3 | 1st | 0.0383 | 0.01915 | 0 | 0 | 0 | 2 | 2 | 0/4 |
| | | | | 2nd | 0 | | 0 | 0 | 0 | 2 | 2 | |
| | | | 506GN4 | 1st | 0.066 | 0.042 | 0 | 2 | 0 | 1 | 3 | 2/5 |
| | | | | 2nd | 0.018 | | 0 | 0 | 0 | 2 | 2 | |
| | | | 506GN5 | 1st | 0.339 | 0.175 | 2 | 1 | 0 | 0 | 3 | 3/5 |
| | | | | 2nd | 0.011 | | 0 | 0 | 0 | 2 | 2 | |
| | | | 506GN6 | 1st | 0.063 | 0.032 | 0 | 0 | 0 | 2 | 2 | 0/4 |
| | | | | 2nd | 0.001 | | 0 | 0 | 0 | 2 | 2 | |
| TTF | Nanog | + | 212B2 | 1st | 0.6613 | 0.52015 | 2 | 1 | 0 | 0 | 3 | 6/6 |
| | | | | 2nd | 0.379 | | 2 | 1 | 0 | 0 | 3 | |
| | | | 212C5 | 1st | 0.5581 | 0.39905 | 3 | 0 | 0 | 0 | 3 | 4/4 |
| | | | | 2nd | 0.24 | | 0 | 1 | 0 | 0 | 1 | |
| | | | 212C6 | 1st | 4.182 | 4.6225 | 3 | 1 | 0 | 0 | 4 | 6/6 |
| | | | | 2nd | 5.063 | | 2 | 0 | 0 | 0 | 2 | |
| | | − | 335D1 | 1st | 0.1593 | 0.09215 | 0 | 0 | 0 | 3 | 3 | 0/5 |
| | | | | 2nd | 0.025 | | 0 | 0 | 0 | 2 | 2 | |
| | | | 335D3 | 1st | 0.01 | 4.4153333 | 0 | 0 | 0 | 2 | 2 | 2/5 |
| | | | | 2nd | 12.829 | | 0 | 1 | 0 | 0 | 1 | |
| | | | | 3rd | 0.407 | | 1 | 0 | 0 | 1 | 2 | |
| | | | 212D1 | 1st | 2.4327 | 2.79885 | 1 | 2 | 0 | 0 | 3 | 5/5 |
| | | | | 2nd | 3.165 | | 1 | 0 | 1 | 0 | 2 | |
| | | | 212D2 | 1st | 1.6079 | 10.61855 | 3 | 0 | 0 | 0 | 3 | 4/4 |
| | | | | 2nd | 19.6292 | | 0 | 1 | 0 | 0 | 1 | |
| | w/o | − | 256H13 | 1st | — | — | 1 | 0 | 1 | 0 | 2 | 2/2 |
| | | | 256H18 | 1st | — | — | 0 | 3 | 0 | 0 | 3 | 4/4 |
| | | | | 2nd | — | | 1 | 0 | 0 | 0 | 1 | |
| | | | 256D4 | 1st | 20.1087 | 10.33805 | 1 | 3 | 0 | 0 | 4 | 7/7 |
| | | | | 2nd | 0.5674 | | 2 | 1 | 0 | 0 | 3 | |
| | | | 256D7 | 1st | 1.6644 | 0.87435 | 2 | 0 | 2 | 0 | 4 | 6/7 |
| | | | | 2nd | 0.0843 | | 1 | 1 | 0 | 1 | 3 | |
| Hep | Nanog | + | 135C4 | 1st | 0.12 | 0.389 | 0 | 0 | 0 | 1 | 1 | 1/5 |
| | | | | 2nd | 1.013 | | 0 | 1 | 0 | 1 | 2 | |
| | | | | 3rd | 0.034 | | 0 | 0 | 0 | 2 | 2 | |
| | | | 135C6 | 1st | 0.975 | 4.6476667 | 0 | 3 | 0 | 0 | 3 | 7/7 |
| | | | | 2nd | 12 | | 1 | 1 | 0 | 0 | 2 | |
| | | | | 3rd | 0.968 | | 2 | 0 | 0 | 0 | 2 | |
| | | | 103C1 | 1st | ND | — | 0 | 0 | 0 | 2 | 2 | 1/5 |
| | | | | 2nd | (carrying | | 1 | 0 | 0 | 0 | 1 | |
| | | | | 3rd | CAG-EGFP) | | 0 | 0 | 0 | 2 | 2 | |
| | | | 103C2 | 1st | ND (carrying CAG-EGFP) | — | 0 | 0 | 0 | 2 | 2 | 0/2 |
| | | − | 390B1 | 1st | Failed to form neurospheres | | | | | | | |
| | | | | 2nd | | | | | | | | |
| | | | | 3rd | | | | | | | | |
| | | | 390B3 | 1st | Failed to form neurospheres | | | | | | | |
| | | | | 2nd | | | | | | | | |

TABLE 3-continued

| | iPS line | | | SNS formation | | Transplantation of SNSs | | | | | |
|---|---|---|---|---|---|---|---|---|---|---|---|
| | | | | | Average of | Diameter of teratoma (mm) | | | | Analyzed | |
| | | | | EGFP+ | EGFP+ | | | | | number of | Teratoma+/ |
| | | | clone's | cells in | cells in | | | | | mice | total |
| Origin | Selection | cMyc | name | Trial | SNSs (%) | SNSs (%) | ≥8.3 | 5.8-8.2 | 0.1-5.7 | 0 | | |
| | Fbx | + | 92A3 | 1st | ND | — | 0 | 0 | 0 | 2 | 2 | 0/6 |
| | | | | 2nd | (carrying | | 0 | 0 | 0 | 3 | 3 | |
| | | | | 3rd | CAG-EGFP) | | 0 | 0 | 0 | 1 | 1 | |
| | | | 98A1 | 1st | ND | — | 0 | 0 | 0 | 2 | 2 | 0/5 |
| | | | | 2nd | (carrying | | 0 | 0 | 0 | 2 | 2 | |
| | | | | 3rd | CAG-EGFP) | | 0 | 0 | 0 | 1 | 1 | |
| | w/o | − | 238C1 | 1st | ND | — | | | | | | |
| | | | | 2nd | | | | | | | | |
| | | | | 3rd | | | | | | | | |
| | | | 238C2 | 1st | 1.625 | 1.1517333 | 0 | 0 | 0 | 2 | 2 | 1/6 |
| | | | | 2nd | 1.2232 | | 0 | 0 | 0 | 2 | 2 | |
| | | | | 3rd | 0.607 | | 1 | 0 | 0 | 1 | 2 | |
| Stm | Fbx | + | 99-1 | 1st | ND | — | 0 | 0 | 0 | 2 | 2 | 0/3 |
| | | | | 2nd | (carrying | | 0 | 0 | 0 | 1 | 1 | |
| | | | | 3rd | CAG-EGFP) | | | | | | | |
| | | | 99-3 | 1st | ND | — | 0 | 0 | 0 | 2 | 2 | 0/5 |
| | | | | 2nd | (carrying | | 0 | 0 | 0 | 2 | 2 | |
| | | | | 3rd | CAG-EGFP) | | 0 | 0 | 0 | 1 | 1 | |
| | | | 116-5 | 1st | ND | — | formed few neurospheres | | | | | |
| | | | | 2nd | (carrying | | | | | | | |
| | | | | 3rd | CAG-EGFP) | | | | | | | |
| | 1A2 Nanog-EGFP-RF8-ES | | 1A2 | 1st | ND | 0.0146667 | 0 | 0 | 0 | 3 | 3 | 0/19 |
| | | | | 2nd | 0 | | 0 | 0 | 0 | 4 | 4 | |
| | | | | 3rd | 0 | | 0 | 0 | 0 | 4 | 4 | |
| | | | | 4th | 0.081 | | 0 | 0 | 0 | 2 | 2 | |
| | | | | 5th | 0 | | 0 | 0 | 0 | 2 | 2 | |
| | | | | 6th | 0 | | 0 | 0 | 0 | 2 | 2 | |
| | | | | 7th | 0.007 | | 0 | 0 | 0 | 2 | 2 | |
| | RF8 | | | 1st | — | — | 0 | 0 | 0 | 2 | 2 | 0/7 |
| | | | | 2nd | — | | 0 | 0 | 0 | 2 | 2 | |
| | | | | 3rd | — | | 0 | 0 | 0 | 3 | 3 | |
| | EB3 | | | 1st | — | — | 0 | 1 | 1 | 2 | 4 | 4/8 |
| | | | | 2nd | — | | 0 | 0 | 0 | 2 | 2 | |
| | | | | 3rd | — | | 0 | 2 | 0 | 0 | 2 | |

TABLE 4

| | iPS line | | | Differentiation in to neural tri-lineage | | | Transplantation of SNSs | | | | Chimera | | |
|---|---|---|---|---|---|---|---|---|---|---|---|---|---|
| | | | | | | Oligo-dendrocyte | | Histology of teratoma | | | | | Germ line trans- |
| | | | clone's | Neuron | Astrocyte | (CNPase+ or | | | | | | | |
| Origin | Selection | cMyc | name | (Tuj1+) | (GFAP+) | O4+) | N | Ectderm | Mesoderm | Endoderm | Embryo | Adult | mission |
| MEF | Nanog | + | 20D17 | + | + | + | 1 | + neural cell | + muscle | + duct | + | + | + |
| | | | 38D2 | + | + | + | | ND | ND | ND | + | + | − |
| | | | 38C2 | + | + | + | — | | | | + | + | − |
| | | | 178B5 | + | + | + | — | | | | + | + | + |
| | | | 178B1 | + | + | + | — | | | | + | + | − |
| | | | 178B2 | + | + | + | — | | | | + | + | − |
| | w/o | − | 506GN1 | ND | ND | ND | — | | | | ND | ND | ND |
| | | | 506GN2 | ND | ND | ND | — | | | | ND | ND | ND |

TABLE 4-continued

| Origin | iPS line Selection | cMyc | clone's name | Differentiation into neural tri-lineage Neuron (Tuj1+) | Astrocyte (GFAP+) | Oligo- dendrocyte (CNPase+ or O4+) | N | Transplantation of SNSs Histology of teratoma Ectderm | Mesoderm | Endoderm | Chimera Embryo | Adult | Germ line trans- mission |
|---|---|---|---|---|---|---|---|---|---|---|---|---|---|
| | | | 506GN3 | ND | ND | ND | — | | | | ND | ND | ND |
| | | | 506GN4 | ND | ND | ND | 1 | + neural cell | − | + duct | ND | ND | ND |
| | | | 506GN5 | ND | ND | ND | 1 | + neural cell | − | + duct | ND | ND | ND |
| | | | 506GN6 | ND | ND | ND | — | | | | ND | ND | ND |
| TTF | Nanog | + | 212B2 | + | + | + | 1 | + neural tube | + cartilage | + duct | + | + | − |
| | | | 212C5 | + | + | + | 1 | + neural tube | + cartilage muscle | + duct | + | + | − |
| | | | 212C6 | + | + | + | 1 | + neural cell | + muscle | + duct | + | + | − |
| | | − | 335D1 | + | + | + | — | | | | + | + | − |
| | | | 335D3 | + | + | + | 1 | + neural cell | + cartilage muscle | + duct | + | + | − |
| | | | 212D1 | + | + | + | 1 | + neural tube keratinized epithelium | +/− adipocyte- | + duct | + | + | − |
| | | | 212D2 | + | + | + | 1 | + neural cell | + cartilage bone | + duct | + | + | − |
| | w/o | − | 256H13 | + | + | + | 1 | + neural tube keratinized epithelium | +/− cartilage- muscle-like | + duct | + | + | − |
| | | | 256H18 | + | + | + | 1 | + neural tube | +/− cartilage- like | + duct | + | + | − |
| | | | 256D4 | + | + | + | 1 | + neural cell keratinized epithelium | + muscle cartilage | + duct | ND | ND | ND |
| | | | 256D7 | + | + | + | 1 | + neural tube keratinized epithelium | + muscle | + duct | ND | ND | ND |
| Hep | Nanog | + | 135C4 | + | + | + | 1 | + neural cell | − | + duct | + | + | − |
| | | | 135C6 | + | + | + | 1 | + neural cell | + cartilage | + duct | + | + | − |
| | | | 103C1 | + | + | + | 1 | + neural cell | + cartilage | + duct | + | + | + |
| | | | 103C2 | + | + | + | — | | | | + | + | − |
| | | | 390B1 | − | − | − | | Failed to form neurospheres | | | ND | ND | ND |
| | | | 390B3 | − | − | − | | Failed to form neurospheres | | | ND | ND | ND |
| | Fbx | + | 92A3 | + | + | + | — | | | | + | + | − |
| | | | 98A1 | + | + | + | — | | | | + | + | − |
| | w/o | − | 238C1 | − | − | − | | | | | ND | ND | ND |
| | | | 238C2 | + | + | + | 1 | + neural cell keratinized epithelium | + bone | + duct | ND | ND | ND |
| Stm | Fbx | + | 99-1 | + | + | + | — | | | | + | + | + |
| | | | 99-3 | + | + | + | | | | | + | + | + |
| | | | 116-5 | + | − | − | | Failed to form neurospheres | | | + | + | − |
| | 1A2 Nanog- EGFP-RF8-ES | | 1A2 | + | + | + | — | | | | | | |
| | | | RF8 | + | + | + | — | | | | | | |
| | | | EB3 | + | + | + | 1 | + neural cell | − | − | | | |

Example 2

Activity of Nanog Promoter

It was examined how many undifferentiated cells are present in the SNSs.

Figure 2:
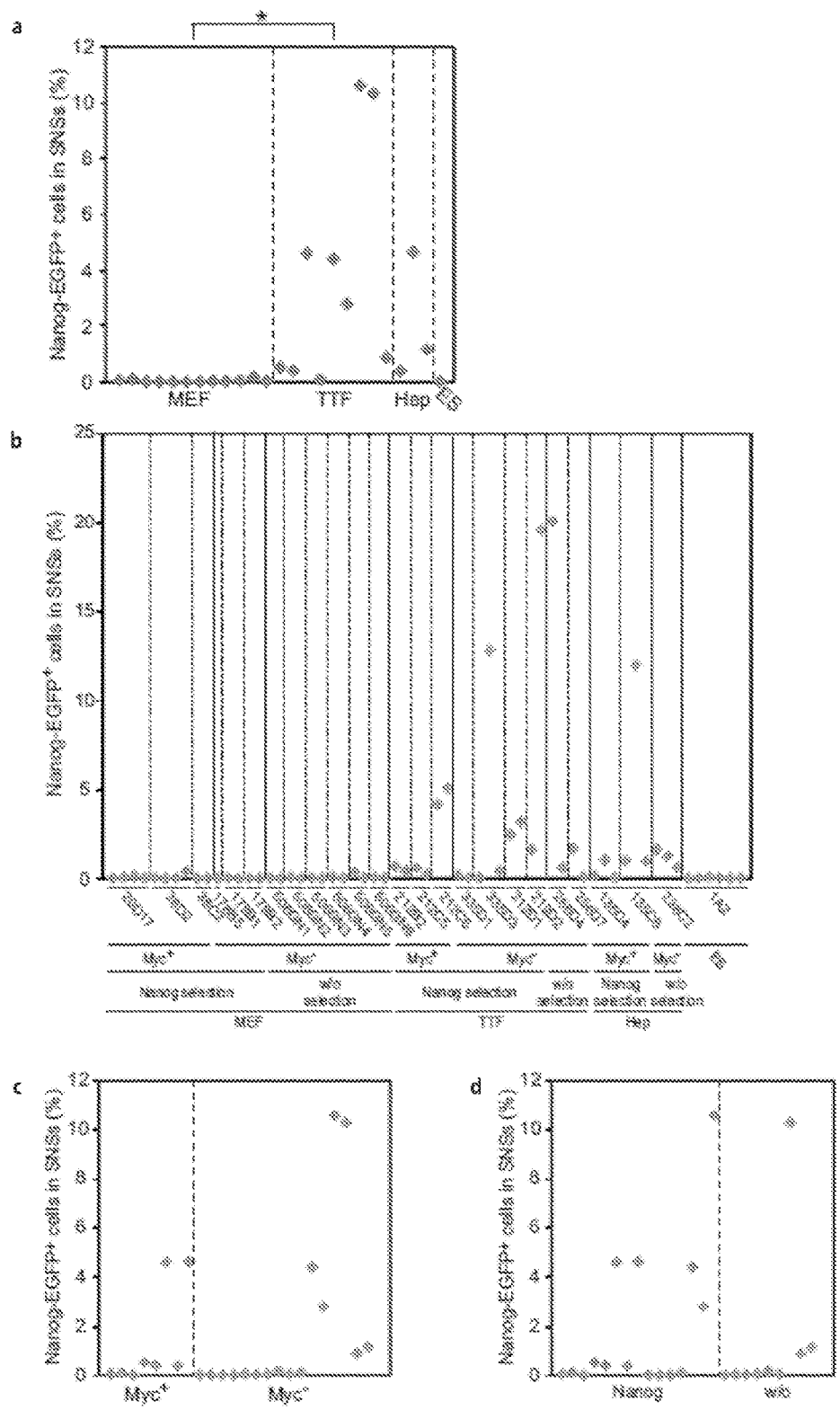
FIG. 2 shows the contents of undifferentiated cells in SNSs derived from ES cells and iPS cells. (a) Comparison of the contents of Nanog-GFP positive cells in SNSs derived from ES cells, MEF-iPS cells, TTF-iPS cells, and Hep-iPS cells. (b) More detailed comparison of the contents of Nanog-GFP positive cells in the SNSs derived from ES cells, MEF-iPS cells, TTF-iPS cells, and Hep-iPS cells. (c) Comparison of the contents of Nanog-GFP positive cells in the SNSs derived from the iPS cells established with or without using Myc. No significant difference was observed in a Mann-Whitney U-test between the respective groups. (d) Comparison of the contents of Nanog-GFP positive cells in the SNSs derived from the iPS cells established with or without selection in terms of expression of Nanog. No significant difference was observed in a Mann-Whitney U-test between respective groups.

In order to evaluate undifferentiated cells by flow cytometer, MEF-iPS cells, TTF-iPS cells, Hep-iPS cells and ES cells, all of them having Nanog-EGFP reporter, were used. These iPS cells have been established in various ways in the presence/absence of c-Myc-containing retrovirus, with/without selection in terms of the expression of Nanog, and the like. The SNSs derived from the MEF-iPS cells contained little or no Nanog-EGFP-positive cell irrespective of the presence of the c-Myc-containing retrovirus or the selection method (0 to 0.38%). This result is similar to that of the ES cell. On the other hand, the SNSs derived from the TTF-iPS cells contained a significantly larger number of Nanog-EGFP-positive undifferentiated cells (0.025 to 20.1%) in comparison to the cells derived from the MEF-iPS cells. The SNSs derived from the Hep-iPS cells also contained a larger number of Nanog-EGFP-positive undifferentiated cells (0.034% to 12.0%) in comparison to the cells derived from the MEF-iPS cells (FIG. 2a and FIG. 2b). The contents of the Nanog-EGFP-positive undifferentiated cells in the SNSs did not show a significant difference irrespective of the presence/absence of the c-Myc-containing retrovirus (FIG. 2c) or the Nanog expression selection (FIG. 2d).

Example 3

Tumor Formation after Transplantation of SNS from Respective iPS Cells

Figure 3:
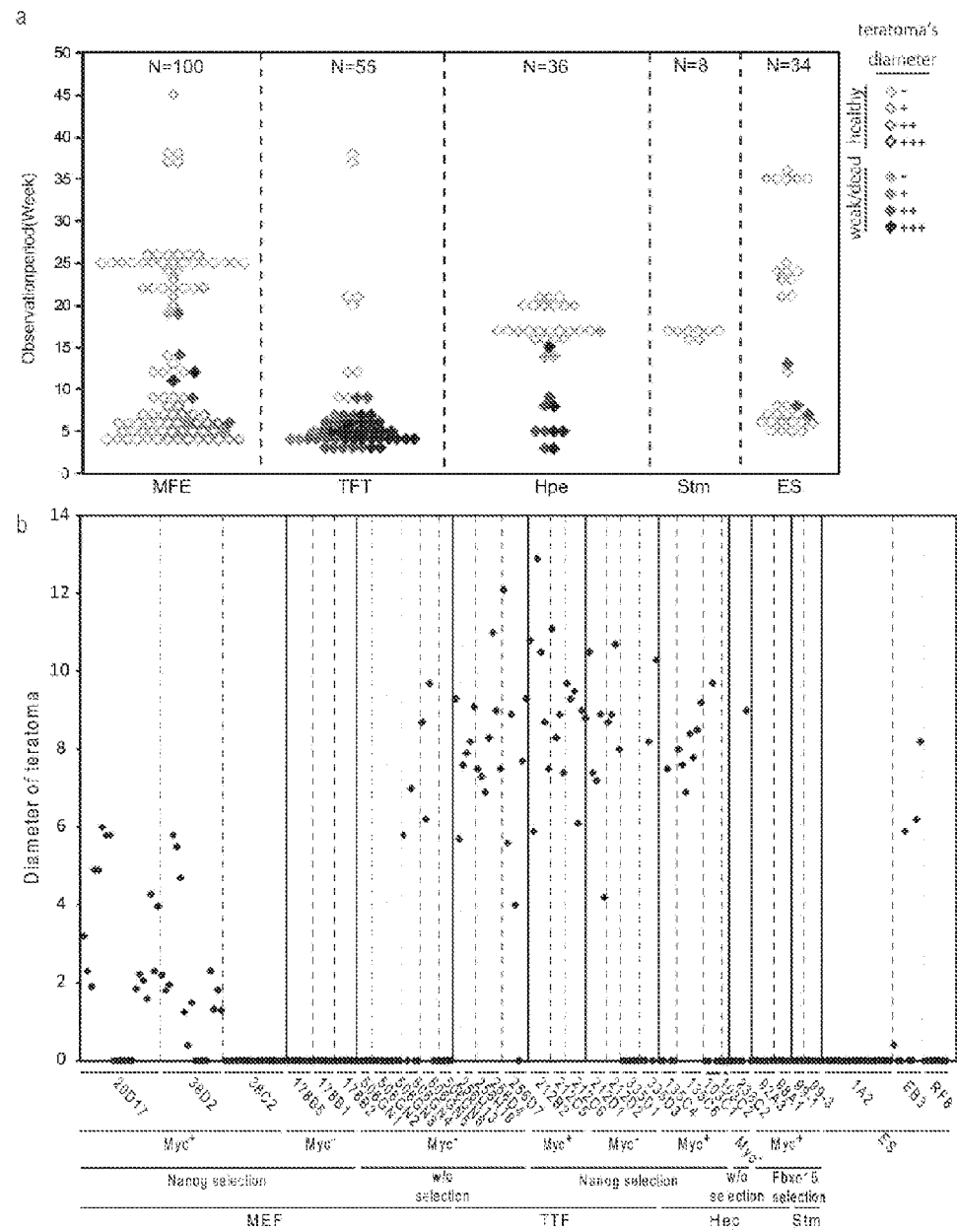
FIG. 3 shows formation of teratomas by the SNSs derived from ES cells or iPS cells. (a) Observation period of transplanted mice divided into four groups according to teratoma formation. A diamond− indicates a mouse without forming teratoma (n=140); a diamond+ indicates a mouse that formed teratoma with a diameter of 0.1 to 5.7 mm (least tertile, n=29); a diamond++ indicates a mouse that formed teratoma with a diameter of 5.8-8.2 mm (second tertile, n=29); and a diamond+++ indicates a mouse that formed teratoma with a diameter of 8.3 mm or more (most tertile, n=29). Filled diamonds indicate dead or weakened mice, whereas open diamonds indicate healthy mice. (b) Diameters of teratomas in the SNSs derived from ES cell clones or iPS cell clones.

In order to evaluate the SNSs derived from ES cells and iPS cells in vivo, the SNSs derived from each of the clones were transplanted into a corpus striatum of a NOD/SCID mouse in which tumor formation was examined (FIG. 3a and FIG. 3b). Mice which died or weakened after the transplantation were then dissected and healthy mice were dissected in 4 to 45 weeks after the transplantation.

Among 34 mice transplanted with SNSs derived from three ES cell clones, three died or weakened by tumor. The remaining 31 mice were also dissected, among which 30 mice did not have a tumor and only one was found to have a small tumor.

On the other hand, among 100 mice transplanted with SNSs derived from 12 MEF-iPS cell clones, nine died or weakened within 19 weeks after the transplantation. Tumor was found in eight of these nine mice. The remaining mice were also dissected, among which 66 mice did not have a tumor, whereas 25 mice showed tumors of various sizes.

Among 55 mice transplanted with SNSs derived from 11 TTF-iPS cell clones, 46 mice died or weakened within 9 weeks after the transplantation. In the remaining nine mice, no tumor was found.

Among 36 mice transplanted with SNSs derived from 7 Hep-iPS cell clones, 13 mice died or weakened within 17 weeks after the transplantation. Tumor was found in 10 of these 13 mice. The remaining 23 mice were also dissected, none of which had a tumor. Further, 8 mice were transplanted with SNSs derived from two Stm-iPS cell clones, in none of which a tumor was observed in 16 weeks after the transplantation.

Figure 4:
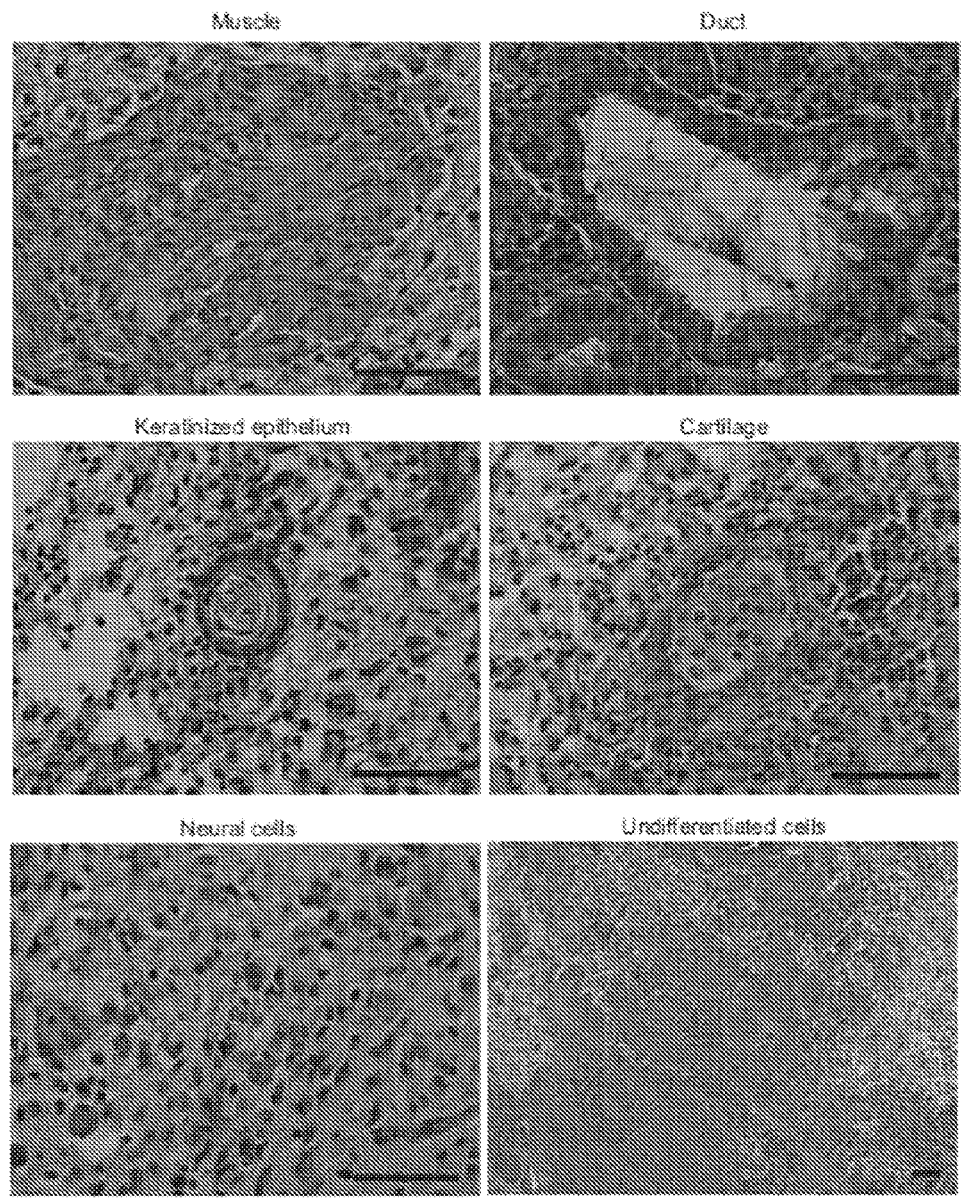
FIG. 4 shows histological images of teratomas generated by SNSs derived from TTF-iPS cells (256D4). Photographs obtained by hematoxylin-eosin staining following formalin fixation, paraffin embedding and sectioning.

Histological analyses showed that these tumors contained various types of cells of endodermal, mesodermal or ectodermal origin, such as epithelial cells of striated muscle or tubular structure, cornified epithelial cells, cartilages and neuronal cells (FIG. 4). Further, the tumors contained large number of undifferentiated cells. Therefore, they are considered to be either teratoma or teratocarcinoma (hereinafter collectively referred to as teratoma). Survival of the transplanted cells was also recognized in normal tissues other than the teratomas in the brain.

Figure 5:
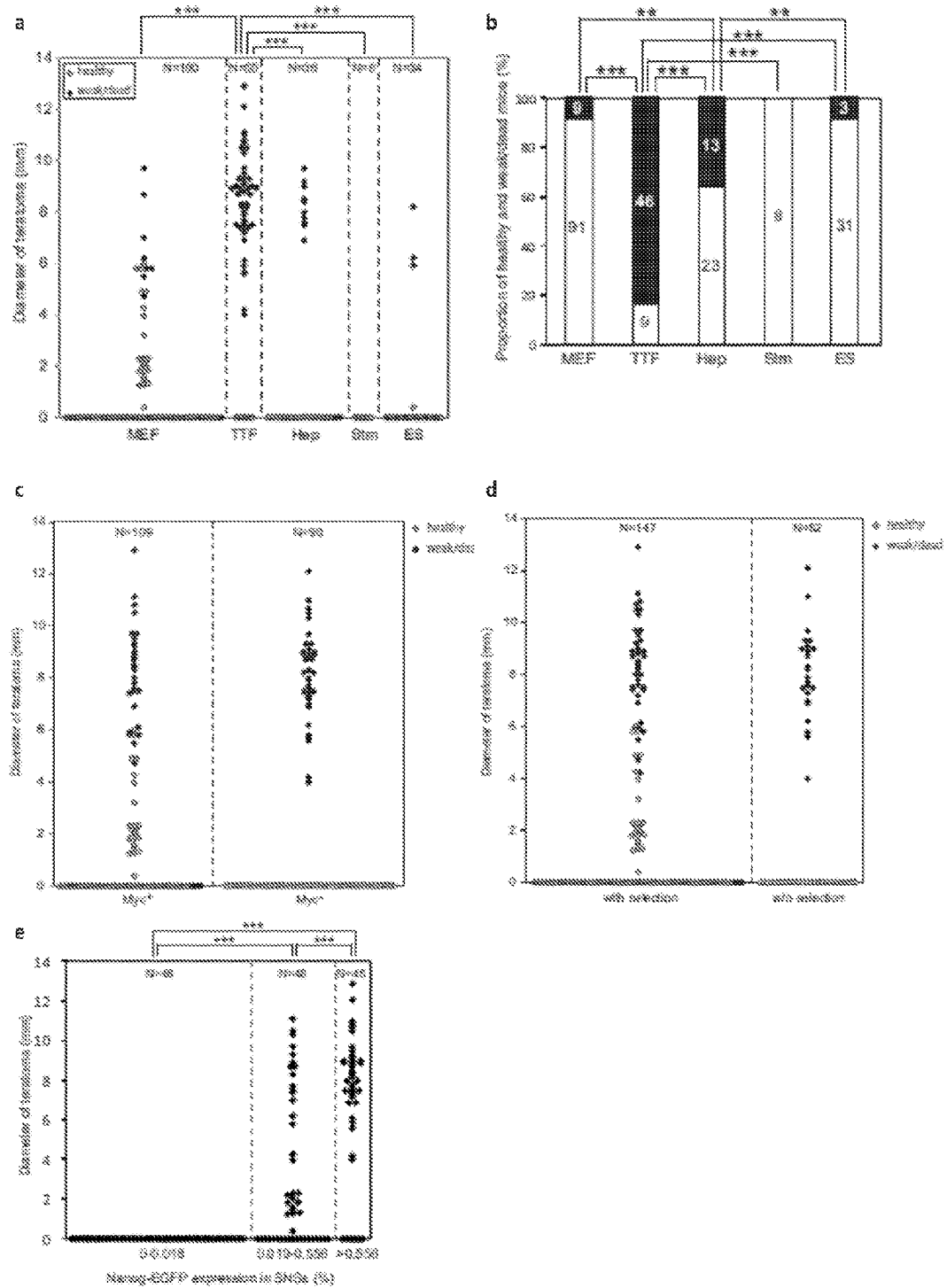
FIG. 5 shows a correlation between the origin of iPS cells and teratoma formation of SNSs. (a) Comparison of diameters of teratomas generated by SNSs derived from MEF-iPS cells, TTF-iPS cells, Hep-iPS cells, Stm-iPS cells or ES cells. Kruskal-Wallis tests and Scheffe tests were employed for the comparison between the respective five groups. * indicates $p<0.0001$. (b) Comparison of ratios of each state of being dead or weakened (in black) and healthy (in white) among the SNSs derived from MEF-iPS cells, TTF-iPS cells, Hep-iPS cells, Stm-iPS cells and ES cells. Chi-square tests were employed for the comparison between the respective two groups.  indicates $p<0.01$ and *** indicates $p<0.0001$. (c) Comparison of diameters of teratomas generated by SNSs derived from iPS cells established with or without using c-Myc. A dead or weakened mouse is indicated by a black diamond, whereas a healthy mouse is indicated by a white diamond. No significant difference was observed in a Mann-Whitney U-test between the respective groups. (d) Comparison of diameters of teratomas generated by SNSs derived from iPS cells established with or without selection. A dead or weakened mouse is indicated by a black diamond, whereas a healthy mouse is indicated by a while diamond. No significant difference was observed in a Mann-Whitney U-test between the respective groups. (e) Correlation between the contents of Nanog positive cells in SNSs and the diameters of teratoma. The mice transplanted with SNSs were divided according to the contents of Nanog-GFP positive cells: (0 to 0.018%, least tertile, 46 mice), (0.019 to 0.556%, second tertile, 48 mice) and (0.556% or more, most tertile, 45 mice).
Figure 6:
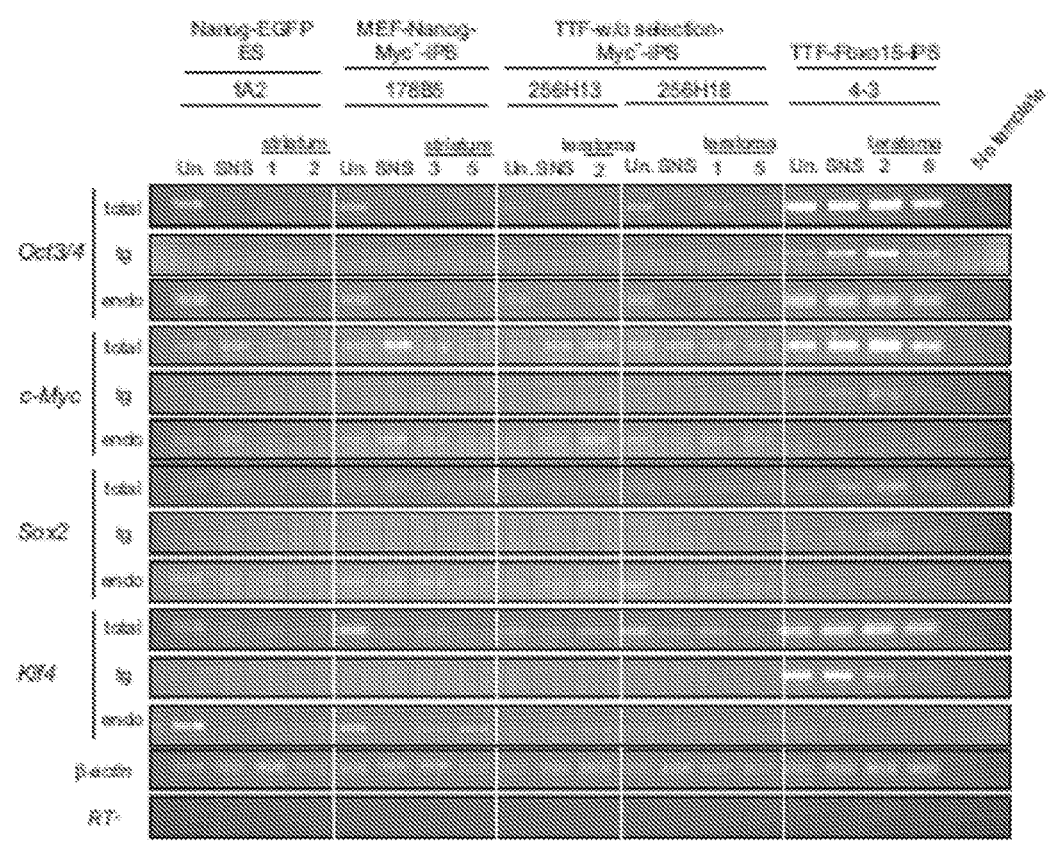

Statistical analyses of these results indicated that the SNSs derived from the TTF-iPS cells formed significantly larger teratoma than the SNSs derived from the other iPS cells or ES cells (FIG. 5a). Further, the SNSs derived from the TTF-iPS cells and the Hep-iPS cells showed significantly larger ratio of died or weakened mice after transplantation (shown in black in the graph) in comparison to the SNSs derived from the other cells (MEF-iPS cell, Stm-iPS cell or ES cells) (FIG. 5b). The use of c-Myc-containing retrovirus (FIG. 5c) or the Nanog expression selection (FIG. 5d) was not significantly relevant with the size of the tumor. In contrast, a significant correlation was found between the diameter of the teratoma and the content of Nanog-EGFP-positive cells in the SNS (FIG. 5e). Although possible contribution of reactivation of the introduced c-Myc-containing retrovirus to tumor formation had been suspected, no reactivation of c-Myc or other introduced gene in the SNS or the teratoma was observed (FIG. 6; the primers used are shown in Table 5).

TABLE 5

| gene name | type | sequence | Seq No |
|---|---|---|---|
| Oct3/4 (endogenous) | sense | TCTTTCCACCAGGCCCCCGGCTC | 1 |
|  | anti-sense | TGCGGGCGGACATGGGGAGATCC | 2 |
| Oct3/4 (exogenous) | sense | TTGGGCTAGAGAAGGATGTGGTTC | 3 |
|  | anti-sense | TTATCGTCGACCACTGTGCTGCTG | 4 |
| c-Myc (endogenous) | sense | TGACCTAACTCGAGGAGGAGCTGGAATC | 5 |
|  | anti-sense | TTATGCACCAGAGTTTCGAAGCTGTTCG | 6 |
| c-Myc (exogenous) | sense | CAGAGGAGGAACGAGCTGAAGCGC | 7 |
|  | anti-sense | TTATCGTCGACCACTGTGCTGCTG | 8 |
| Sox2 (endogenous) | sense | TAGAGCTAGACTCCGGGCGATGA | 9 |
|  | anti-sense | TTGCCTTAAACAAGACCACGAAA | 10 |
| Sox2 (exogenous) | sense | GGTTACCTCTTCCTCCCACTCCAG | 11 |
|  | anti-sense | TTATCGTCGACCACTGTGCTGCTG | 12 |

TABLE 5-continued

| gene name | type | sequence | Seq No |
|---|---|---|---|
| Klf4 (endogenous) | sense | CCAACTTGAACATGCCCGGACTT | 13 |
| | anti-sense | TCTGCTTAAAGGCATACTTGGGA | 14 |
| Klf4 (exogenous) | sense | GCGAACTCACACAGGCGAGAAACC | 15 |
| | anti-sense | TTATCGTCGACCACTGTGCTGCTG | 16 |
| β-actin | sense | CGTGGGCCGCCCTAGGCACCA | 17 |
| | anti-sense | TTGGCCTTAGGGTTCAGGGGG | 18 |

Example 4

Activity of Nanog Promoter in Subclone

To understand the reason of occurring partial differentiation in one iPS cell clone, subclones were established from 4 iPS cell clones, each of which had different background, and an ES cell line as control (Table 6 to 10).

TABLE 6

| iPS line | | | | SNS formation GFP+ cells in SNSs (%) | |
|---|---|---|---|---|---|
| Origin | Selection | cMyc | clone's name | sub clone's | 1st | 2nd |
| TTF | Nanog | + | 212C6 | parent | 1.592 | 1.472 |
| | | | | #3 | 0.015 | 0.254 |
| | | | | #5 | 4.551 | 6.27 |
| | | | | #6 | 36.754 | 21.121 |
| | | | | #10 | 18.899 | 0.79 |
| | | | | #11 | 0.038 | 0.223 |
| | | | | #12 | — | 16.977 |
| | | | | #13 | 0.002 | 0.042 |
| | | | | #14 | 44.962 | 38.719 |
| | | | | #17 | 33.005 | 20.59 |
| | | | 1A2 | | 0 | 0.001 |

TABLE 7

| iPS line | | | | SNS formation GFP+ cells in SNSs (%) | | |
|---|---|---|---|---|---|---|
| Origin | Selection | cMyc | clone's name | sub clone's | 1st | 2nd | 3rd |
| TTF | w/o | − | 256D4 | parent | 2.64 | 10.238 | 35.47 |
| | | | | #1 | 6.485 | — | — |
| | | | | #2 | 4.025 | — | — |
| | | | | #3 | 3.509 | — | — |
| | | | | #4 | 5.026 | — | — |
| | | | | #5 | 4.999 | — | — |
| | | | | #6 | 16.544 | — | — |
| | | | | #7 | 5.245 | — | — |
| | | | | #8 | 22.13 | — | — |
| | | | | #9 | 24.755 | — | — |
| | | | | #10 | 3.598 | — | — |
| | | | | #32 | — | 0.004 | 0.049 |
| | | | | #33 | — | 0.045 | 0.079 |
| | | | | #34 | — | 6.424 | 8.354 |
| | | | | #36 | — | 38.339 | 41.689 |
| | | | | #39 | — | 12.032 | 18.794 |
| | | | | #41 | — | 0.639 | 3.114 |
| | | | | #45 | — | 17.782 | 17.289 |
| | | | | #47 | — | 0.034 | 0.013 |
| | | | | #48 | — | 22.438 | 1.303 |
| | | | 1A2 | | 0.001 | 0 | 0.034 |

TABLE 8

| iPS line | | | | SNS formation GFP+ cells in SNSs (%) | |
|---|---|---|---|---|---|
| Origin | Selection | cMyc | clone's name | sub clone's | 1st | 2nd |
| Hep | Nanog | + | 135C6 | parent | 2.45 | 0.156 |
| | | | | #13 | 0.483 | 0.007 |
| | | | | #26 | 0.053 | 0 |
| | | | | #28 | 0.427 | 0.038 |
| | | | | #29 | 0.268 | 0.005 |
| | | | | #30 | 8.051 | 0.351 |
| | | | | #37 | 11.684 | 0.658 |
| | | | | #40 | 10.242 | 3.519 |
| | | | | #44 | 8.445 | 0.79 |
| | | | | #48 | 1.307 | 0.024 |
| | | | 1A2 | | 0.017 | 0 |

TABLE 9

| iPS line | | | | SNS formation GFP+ cells in SNSs (%) | |
|---|---|---|---|---|---|
| Origin | Selection | cMyc | clone's name | sub clone's | 1st | 2nd |
| MEF | Nanog | − | 178B5 | parent | 0 | 0.005 |
| | | | | #1 | 0 | 0.001 |
| | | | | #2 | 0.002 | 0 |
| | | | | #3 | 0 | 0.003 |
| | | | | #4 | 0 | 0.01 |
| | | | | #5 | 0.009 | 0 |
| | | | | #6 | 0 | 0.001 |
| | | | | #7 | 0.003 | 0.001 |
| | | | | #8 | 0 | 0.047 |
| | | | | #9 | 0 | 0.022 |
| | | | | #10 | 0.001 | 0.002 |
| | | | 1A2 | | 0 | 0.034 |

TABLE 10

| ES line | | SNS formation GFP+ cells in SNSs (%) | |
|---|---|---|---|
| | sub clone's | 1st | 2nd |
| 1A2 | parent | 0 | 0.015 |
| | #1 | 0 | 0.036 |
| | #2 | 0 | 0.014 |
| | #3 | 0 | 0 |
| | #4 | 0 | 0.002 |
| | #5 | 0 | 0.001 |
| | #6 | 0 | 0.007 |
| | #7 | 0 | 0.051 |
| | #8 | 0.001 | 0.017 |
| | #9 | 0.001 | 0.029 |
| | #10 | 0 | 0 |

Undifferentiated cells in SNSs derived from the subclones of iPS cell lines were evaluated with GFP expression substituted for Nanog expression by using flow cytometer. Then some subclones contained lower content of GFP positive cells but very few subclones contained higher content than the parent cell lines (212C6, 256D4 and 135C6) which were contained a substantial number of undifferentiated cells after formation of SNSs. On the other hand, there were little GFP positive cells in subclones from 178B5 which hardly contained undifferentiated cells after formation of SNSs and here also very few subclones contained higher content than the parent cell line. It has been thus confirmed that the clones have a tendency of reducing the content of GFP-positive cells during passages.

Accordingly since the clones do not gain new potential of resistant against induction of differentiation, the content of the undifferentiated cells in a clone of iPS cells, which is measured at a certain time point, is useful for judging the tumor formation rate that an offspring of the clone inherently has.

Example 5

Standard Value for Evaluation of iPS Cell Lines

There was a significant correlation between the occurrence of tumorigenesis and the content of Nanog-positive cells in the SNSs; hence the content of the Nanog-positive cells might be useful for prospective evaluation of tumorigenecity by transplantation of the SNSs derived from iPS cells. When a certain control value of percentage of the content is set, the sensitivity and specificity for judgement as catching the tumorigenesis are shown in Table 11.

TABLE 11

| iPS line clone's name | SNS formation | | Transplantation of SNSs Teratoma+/ total | Evaluation by tumor formation | Evaluation by maximum value (control maximum value) | | | | |
|---|---|---|---|---|---|---|---|---|---|
| | EGFP+ cells in SNSs (%) | Average of EGFP+ cells in SNSs (%) | | | (.0.082%) | (.0.066%) | (0.051%) | (0.019%) | (0.042%) |
| 20D17 | 0.00363 0.049 0.11 0.019 | 0.0454075 | 15/21 | + | + | + | + | + | + |
| 38D2 | 0.026 0.00143 0.00779 0.38 | 0.103805 | 13/17 | + | + | + | + | + | + |
| 38C2 | 0 0 | 0 | 0/17 | − | − | − | − | − | − |
| 178B5 | 0 | 0 | 0/7 | − | − | − | − | − | − |
| 178B1 | 0.0012 0 | 0.0006 | 0/6 | − | − | − | − | − | − |
| 178B2 | 0.0012 0 | 0.0006 | 0/6 | − | − | − | − | − | − |
| 506GN1 | 0.0052 0 | 0.0026 | 0/4 | − | − | − | − | − | − |
| 506GN2 | 0.0719 0.002 | 0.03695 | 0/4 | − | − | + | + | + | − |
| 506GN3 | 0.0383 0 | 0.01915 | 0/4 | − | − | − | − | + | − |
| 506GN4 | 0.066 0.018 | 0.042 | 2/5 | + | − | + | + | + | + |
| 506GN5 | 0.339 0.011 | 0.175 | 3/5 | + | + | + | + | + | + |
| 506GN6 | 0.063 0.001 | 0.032 | 0/4 | − | − | − | + | + | − |
| 212B2 | 0.6613 0.379 | 0.52015 | 6/6 | + | + | + | + | + | + |
| 212C5 | 0.5581 0.24 | 0.39905 | 4/4 | + | + | + | + | + | + |
| 212C6 | 4.182 5.063 | 4.6225 | 6/6 | + | + | + | + | + | + |
| 335D1 | 0.1593 0.025 | 0.09215 | 0/5 | − | + | + | + | + | + |
| 335D3 | 0.01 12.829 0.407 | 4.41533333 | 2/5 | + | + | + | + | + | + |
| 212D1 | 2.4327 3.165 | 2.79885 | 5/5 | + | + | + | + | + | + |
| 212D2 | 1.6079 19.6292 | 10.61855 | 4/4 | + | + | + | + | + | + |
| 256D4 | 20.1087 0.5674 | 10.33805 | 7/7 | + | + | + | + | + | + |
| 256D7 | 1.6644 0.0843 | 0.87435 | 6/7 | + | + | + | + | + | + |
| 135C4 | 0.12 1.013 0.034 | 0.389 | 1/5 | + | + | + | + | + | + |

TABLE 11-continued

| iPS line clone's name | EGFP+ cells in SNSs (%) | Average of EGFP+ cells in SNSs (%) | of SNSs Teratoma+/ total | Evaluation by tumor formation | Evaluation by maximum value (control maximum value) | | | | |
|---|---|---|---|---|---|---|---|---|---|
| | | | | | (.0.082%) | (.0.066%) | (0.051%) | (0.019%) | (0.042%) |
| 135C6 | 0.975<br>12<br>0.968 | 4.64766667 | 7/7 | + | + | + | + | + | + |
| 238C2 | 1.625<br>1.2232<br>0.607 | 1.15173333 | 1/6 | + | + | + | + | + | + |
| 1A2 | 0<br>0<br>0.081<br>0<br>0<br>0.007 | 0.0176 | 0/19 | − | − | + | + | + | − |
| | sensitivity | | | | 0.93 | 1 | 1 | 1 | 1 |
| | specificity | | | | 0.9 | 0.7 | 0.6 | 0.5 | 0.9 |

The high sensitivity shows low degree of false negative of the judgement, and the high specificity shows low degree of false positive of the judgement. The control maximum value was used in the case of comparing the maximum value among results of a plurality of trials. Similarly, the control average value was used in the case of comparing the average of results of a plurality of trials. The control maximum value of 0.082% was determined by using value of ES cells as a control known not to substantially cause tumor formation. The control maximum value of 0.066% was determined by using value of 506GN4, because the value is the minimum highest value in the case of tumorigenesis. The control maximum value of 0.051% was determined by using value of 1A2 subclone case (shown in Table 10) as a control known not to substantially cause tumor formation. The control maximum value of 0.019% was useful, because a significant correlation was found between the diameter of the teratoma and the SNS with the content of Nanog-EGFP-positive cells more than 0.019% (FIG. 5e). The control average value of 0.042% was determined by using value of 506GN4, because the value is the lowest maximum value in the case of tumorigenesis. It should be noted that, in Table 11, "+" shows tumorigenesis for evaluation by tumor formation and over the control value for evaluation by maximum value, and "−" shows no tumorigenesis and under the control value. There were some false judgments for evaluating tumorigenesis by using the control maximum value, but the reliability of the judgment is very high.

To summarize, an induction of differentiation into neural cells in vitro has been confirmed to be a sensitive method for evaluating iPS cell clones and subclones.

The invention claimed is:

1. A method for selecting induced pluripotent stem cells (iPS cells) comprising:
   (1) providing iPS cell clones,
   (2) differentiating the iPS cell clones into neurospheres,
   (3) measuring the percentage of cells that express Nanog gene in the neurospheres, and
   (4) selecting iPS cell clones corresponding to neurospheres measured in step (3) having decreased percentage of cells expressing Nanog as compared to neurospheres obtained from embryonic stem (ES) or iPS cell clones known not to cause tumor formation when differentiated and transplanted into a living body.

2. The method according to claim 1, wherein less than 0.042% of the cells of the neurospheres corresponding to the iPS cell clones selected in step (4) express Nanog gene, based on an average value from multiple measurements.

3. The method according to claim 1, wherein less than 0.066% of the cells of the neurospheres corresponding to the iPS cell clones selected in step (4) express Nanog gene, based on a maximum value from multiple measurements.

4. The method according to claim 1, wherein the iPS cell clones have been established by introducing genes comprising Oct3/4 gene, Sox2 gene, and Klf4 gene, or Oct3/4 gene, Sox2 gene, Nanog gene, and Lin28 gene.

* * * * *